(12) United States Patent
Kendrick

(10) Patent No.: US 11,517,481 B2
(45) Date of Patent: Dec. 6, 2022

(54) THERAPEUTIC TAPE

(71) Applicant: PosturePals Pty Ltd, Port-Vila (VU)

(72) Inventor: Ryan Kendrick, Golden Beach (AU)

(73) Assignee: PosturePals Pty Ltd, Port-Vila (VU)

( * ) Notice: Subject to any disclaimer, the term of this patent is extended or adjusted under 35 U.S.C. 154(b) by 366 days.

(21) Appl. No.: 15/555,673

(22) PCT Filed: Mar. 6, 2016

(86) PCT No.: PCT/AU2016/050156
§ 371 (c)(1),
(2) Date: Sep. 5, 2017

(87) PCT Pub. No.: WO2016/141426
PCT Pub. Date: Sep. 15, 2016

(65) Prior Publication Data
US 2018/0042775 A1    Feb. 15, 2018

(30) Foreign Application Priority Data

Mar. 6, 2015    (AU) ................................ 2015900806

(51) Int. Cl.
*A61F 13/00*    (2006.01)
*A61F 13/02*    (2006.01)
(Continued)

(52) U.S. Cl.
CPC .... *A61F 13/0246* (2013.01); *A61F 13/00059* (2013.01); *A61F 13/0236* (2013.01);
(Continued)

(58) Field of Classification Search
CPC .............. A61F 13/0246; A61F 13/0259; A61F 13/0269; A61F 13/0273; A61F 13/0276;
(Continued)

(56) References Cited

U.S. PATENT DOCUMENTS 3,077,006 A    2/1963 Ibrahim
3,460,338 A    8/1969 Morrison
(Continued)

FOREIGN PATENT DOCUMENTS

EP    2371331 B1    12/2012

OTHER PUBLICATIONS

"Recycled Spandex Eco-Friendly, SP-ECO91 EcoGreen Yarn Spandex Wicking—Anti Microbial (spandexbyyard.com)" [retrieved from Internet May 6, 2016]. URL: <http://spandexbyyard.com/back/0/category/Eco_Friendly_Recycled_Spandex/name/SP-ECO91-EcoGreen-Yarn-Spandex-Wicking-Anti-Microbial/pid/379/stylecode/speco91.html> [Published on Nov. 17, 2014 as per Wayback Machine].

(Continued)

*Primary Examiner* — Adam Baker
(74) *Attorney, Agent, or Firm* — Hamilton, Brook, Smith & Reynolds, P.C.

(57) ABSTRACT

The invention relates to a therapeutic adhesive tape for use in medical or sporting applications. The therapeutic tape is configured to be applied to the skin of a user. The tape comprising: a base layer having a face side and a back side, the base layer being composed of a combination of recycled
(Continued)

polyethylene terephthalate (hereinafter: RPET) and an elastic material, and an adhesive layer deposited on one of said face side or back side of the base layer for attaching the tape to the skin of the user.

21 Claims, 6 Drawing Sheets

(51) Int. Cl.
*A61L 15/58* (2006.01)
*A61L 15/26* (2006.01)
*A61F 13/06* (2006.01)
*A61L 15/22* (2006.01)
*B32B 5/02* (2006.01)
*B32B 7/06* (2019.01)
*B32B 7/12* (2006.01)
*B32B 27/36* (2006.01)

(52) U.S. Cl.
CPC .......... *A61F 13/0259* (2013.01); *A61F 13/06* (2013.01); *A61L 15/225* (2013.01); *A61L 15/26* (2013.01); *A61L 15/58* (2013.01); *B32B 5/024* (2013.01); *B32B 7/06* (2013.01); *B32B 7/12* (2013.01); *B32B 27/36* (2013.01); *B32B 2535/00* (2013.01)

(58) Field of Classification Search
CPC .... A61F 13/00059; A61F 13/00; A61F 13/10; A61F 13/143; A61F 13/146; A61F 13/00034; A61F 13/08; A61F 5/00; A61F 5/40; A61F 5/0102; A61F 5/0104; A61F 5/0109; A61F 5/0118; A61F 5/028; A61F 5/05883; A61F 5/05808; A61F 5/05; A61F 5/04; A61F 5/013
USPC .......................................................... 602/60
See application file for complete search history.

(56) References Cited

U.S. PATENT DOCUMENTS

| | | | | |
|---|---|---|---|---|
| 4,665,909 A | * | 5/1987 | Trainor | A61F 13/0273 602/75 |
| 4,679,554 A | * | 7/1987 | Markham | A61F 5/40 602/70 |
| 4,737,400 A | | 4/1988 | Edison et al. | |
| 4,747,400 A | | 4/1988 | Edison et al. | |
| 5,006,401 A | * | 4/1991 | Frank | A61F 13/0273 442/151 |
| 5,397,298 A | * | 3/1995 | Mazza | A61F 13/00991 602/41 |
| 5,779,659 A | * | 7/1998 | Allen | A61F 13/00038 602/75 |
| 5,861,348 A | * | 1/1999 | Kase | A61F 13/025 442/184 |
| 2001/0047144 A1 | * | 11/2001 | Tillotson | A61F 13/00059 602/41 |
| 2006/0253058 A1 | * | 11/2006 | Evans | A61F 13/0273 602/41 |
| 2011/0276040 A1 | * | 11/2011 | Quinn | A61F 5/40 606/1 |
| 2013/0177264 A1 | * | 7/2013 | Utterback | A45C 3/001 383/117 |

OTHER PUBLICATIONS

Trufusion, "Activewear Technology: Why sweating in sweats doesn't work," published Feb. 6, 2015 [retrieved from Internet May 13, 2016]. URL: <https://trufusion.com/blog/activewear-technology-why-sweating-in-sweats-doesnt-work/>.
International Preliminary Report of Patentability, International Patent Application PCT/AU2016/050156 (completed Feb. 2, 2017).

* cited by examiner

THERAPEUTIC TAPE

FIELD OF THE INVENTION

The invention relates to a therapeutic adhesive tape for use in medical or sporting applications.

BACKGROUND OF THE INVENTION

Elastic therapeutic tapes are used for relieving pain from athletic injuries and a variety of other physical disorders. Typically, elastic therapeutic tapes such as Kinesiology tapes are designed to mimic the human skin. The elastic property of the tape creates a pulling force on the skin when applied. This pulling force is claimed to facilitate or inhibit muscle activity to alter joint motion, correct alignment of weak muscles and lift the skin to increase blood flow and reduce tissue pressure and pain perception. The tape is usually applied with the affected muscle in a stretched position and is primarily claimed to work via changes resulting from the neurophysiological input into the nervous system due to the contact with the tape on the skin.

Elastic therapeutic tapes on the market are generally designed around a kinesiology taping philosophy of going on with the muscle on stretch and with varying degrees of stretch of the tape depending on the application. The two-way (longitudinal only) stretching tapes are either 100% cotton or may include 3-5% nylon. These tapes can generally stretch to about 140-180% of their relaxed length and do not stretch transversely which often creates limitation on the athlete when performing complex movements. If full range of movement of a muscle is required, the tape has to be applied with the muscle in a stretched position. This reduces the effectiveness of the recoil properties of the tape. If applied in the shortened position of the muscle, the rigid ends of the tape cause the tape to run out of stretch before the muscle can fully extend. The tape will then come off or restrict motion, often causing blisters due to traction on the skin.

Furthermore, current therapeutic tape technology exhibits weak recoil and therefore often fails to provide the required level of deceleration of motion to mechanically assist the muscle and connective tissue in their required functions. The tape also often significantly reduces in recoil force after a few repetitions of stretch. The materials used for producing these tapes can also place significant strain on the environment as cotton is a water intensive material and relies on many harmful chemicals during processing.

The current therapeutic tape design and philosophy therefore exhibits a number of disadvantages.

Clearly it would be advantageous to provide an improved elastic therapeutic tape that alleviates at least some of the abovementioned disadvantages of current therapeutic tape technology, or to at least provide the public with a useful choice.

SUMMARY OF THE INVENTION

In a first aspect the invention may broadly be said to consist of a therapeutic tape configured to be applied to the skin of a user, the tape comprising:

a base layer having a face side and a back side, the base layer being composed of a combination of Recycled Polyethylene terephthalate (hereinafter: RPET) and an elastic material, and an adhesive layer deposited on one of said face side or back side of the base layer for attaching the tape to the skin of the user.

Preferably the elastic material is spandex.

Preferably the tape is stretchable along at least two dimensions. Preferably the tape is stretchable in both directions along a longitudinal axis of the tape stretchable in both directions along a transverse axis of the tape.

Preferably the tape is stretchable to approximately 190% of a relaxed length of the tape.

Preferably the base layer is woven. More preferably the base layer is weft woven.

In one embodiment the tape further comprises a release liner configured to cover an exposed surface of the adhesive layer when the tape is not in use.

Preferably the base layer comprises of a density of between approximately 180 gsm and approximately 320 gsm, more preferably between approximately 220 gsm and approximately 300 gsm, and most preferably between approximately 280 gsm and approximately 290 gsm.

Preferably the base layer comprises between approximately 70% and 95% of RPET, more preferably between approximately 80% and approximately 90% of RPET and most preferably approximately 83% of RPET.

Preferably the base layer comprises between approximately 5% and 30% of spandex, more preferably between approximately 10% and approximately 20% of spandex and most preferably approximately 17% of spandex.

Preferably the base layer is formed from a yarn of RPET of a grade of between approximately 50D and approximately 120D, more preferably between approximately 65D and approximately 105D and most preferably approximately 100D.

Preferably the base layer is formed from a yarn of spandex of a grade of between approximately 20D and approximately 60D, more preferably between approximately 30D and approximately 50D and most preferably approximately 40D.

In one embodiment, the tape is an elongate strip of material. The elongate strip of material may be wound into a roll in the unused state. In alternative embodiments the tape is a planar sheet of material preformed to a desired shape and/or configured to be cut to a desired shape for use.

Preferably the base layer comprises a printed ink design deposited on a side the base layer configured to be exposed in use.

Preferably the layer of adhesive is deposited on the face side of the base layer.

In a second aspect the invention may broadly be said to consist of a method of manufacturing a therapeutic tape comprising the steps of:

forming a base layer of fabric by weaving a recycled polyethylene terephthalate (RPET) material with an elastic material, and depositing a layer of adhesive on either a face side or a back side of the formed base layer.

Preferably the method further comprises the step of adhering a release liner on the layer of adhesive for covering the layer of adhesive.

Preferably the step of weaving comprises weft weaving the RPET material with the elastic material.

Preferably the method further comprises the step of printing an ink on a side of the base layer opposing the side to which the adhesive is deposited.

Preferably the method further comprises the step of winding the tape into a roll.

In accordance with a further aspect, the invention may broadly be said to consist of a therapeutic tape configured to be applied to the skin of a user, the tape comprising: a base layer having a face side and a back side, the base layer being a woven layer with two sets of yarns or threads interlaced at right angles to form the base layer, the yarns or threads being composed of a combination of recycled polyethylene terephthalate (hereinafter: RPET), a fabric material and an elastic material, and an adhesive layer deposited on one of said face side or back side of the base layer for attaching the tape to the skin of the user.

Preferably, the fabric material may consist of intermittent threads interlaced into the base layer between the RPET and the elastic material, the threads of fabric material ensure that the base layer maintains a predetermined width while allowing an increase in the elastic recoil of the tape.

Preferably, the tape may be stretchable along at least two dimensions. Preferably, the tape may be stretchable in both directions along a longitudinal axis of the tape and stretchable in both directions along a transverse axis of the tape. The tape may be stretchable to approximately 190% of a relaxed length of the tape.

Preferably, the base layer may be woven in the form of a twill style textile weave. Alternatively, the base layer may be weft woven.

Preferably, the tape may further comprise a release liner configured to cover an exposed surface of the adhesive layer when the tape is not in use.

Preferably, the elastic material may be spandex.

Preferably, the fabric material may be any man-made or synthetic fibres.

Any one or more of the above embodiments or preferred features can be combined with any one or more of the above aspects.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

The phrase "mechanical advantage" as used in this specification and claims in relation to a levered system means the ratio of the moment arm through which an applied force acts to the moment arm through which a resistive force acts.

The term "spandex" as used in this specification and claims means an elastic synthetic fibre composed of a polyester-polyurethane copolymer and includes within its definition other terms for an elastic synthetic fibre such as "lycra" and "elastane".

As used herein the term "and/or" means "and" or "or", or both.

As used herein "(s)" following a noun means the plural and/or singular forms of the noun.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF THE PREFERRED EMBODIMENTS

Figure 1:
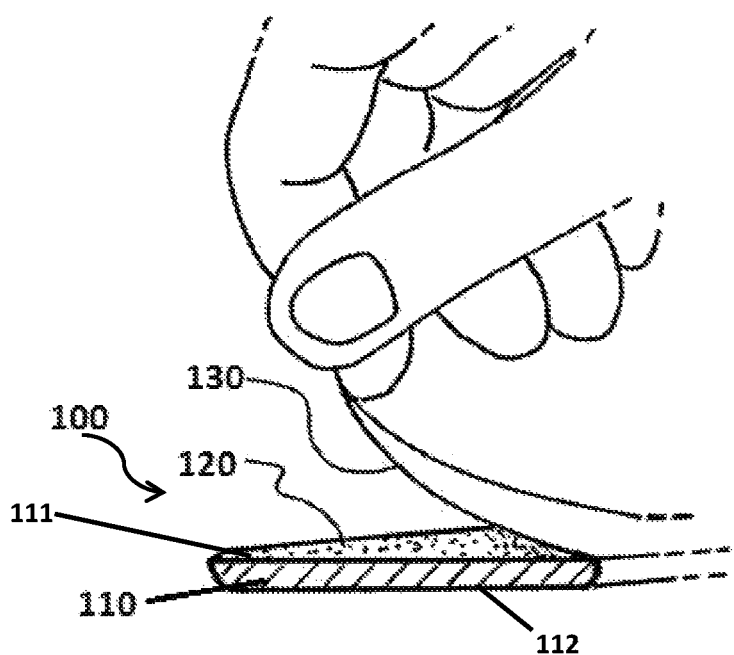
FIG. 1 is a perspective view of a preferred form therapeutic tape of the invention.

Referring to FIG. 1, a preferred form therapeutic tape 100 of the invention is shown comprising a base layer 110 and an adhesive layer 120 deposited on a surface/side 111 of the base layer 110. An optional thin and removable sheet of material (release liner) 130 may be provided over the adhesive layer 120 during manufacturing of the tape 100 for covering and protecting the adhesive layer 120 prior to application. The therapeutic tape 100 of the invention has been designed to facilitate mechanical movement by providing mechanical compensation as well as physiological support.

The therapeutic tape 100 is configured to be attached to the skin of an athlete or user along and/or across one or more muscles or musculotendinous units of the body. The tape 100 is stretchable and resilient to support and/or facilitate the user's movement in the appropriate manner as will be described in detail below.

The therapeutic tape 100 may take on any number of forms or shapes in accordance with the required region of application. In one embodiment the tape 100 may be formed as a roll of tape 100 from which a user may cut any desired length. Alternatively, the tape 100 may be pre-formed to have a particular shape such as a cross shape or Y-shape to extend over a desired region of the user's body. In yet another alternative, the therapeutic tape 100 may be formed as a planar sheet of fabric from which one or more sections of the tape may be cut to desired shapes depending on the application.

Composition

The base layer 110 of the therapeutic tape 100 is composed of a combination of materials that give it a set of properties particularly useful in enhancing athletic performance and/or supporting injured or disabled muscles of a user. The base layer 110 is substantially deformable and stretchable but sufficiently elastic along at least one axis. In the preferred embodiment the base layer is elastic along two substantially orthogonal axes. For example, in the case where the therapeutic tape is an elongate strip of material (cut from a roll of tape for instance) the tape is elastic in both directions over at least a longitudinal axis of the tape, and in the preferred embodiment also elastic in both directions along a substantially orthogonal transverse axis of the tape. In other words the tape is stretchable in four orthogonal directions along the major plane of a major face of the tape.

To give it its stretchable and elastic properties, the base layer 110 is composed of an elastic material such as an elastomer and/or a stretchable fabric. In the preferred embodiment, the base layer is composed of a spandex fabric. The base material 110 is further composed of a Polyethylene terephthalate (PET) fabric and most preferably a Recycled PET (RPET) fabric. RPET has a higher tensile strength and modulus of elasticity than virgin PET.

As mentioned above, to achieve the desired level of elasticity the base layer 110 is preferably composed of a combination of RPET and spandex. In the preferred embodiment, the base layer 110 comprises between approximately 95.0% and approximately 70% by weight of RPET and between 5.0% and approximately 30% by weight of spandex, more preferably between approximately 90.0% and approximately 80.0% by weight of RPET and between approximately 10.0% and approximately 20.0% by weight of spandex, and most preferably approximately 83.0% by weight of RPET and approximately 17.0% by weight of spandex.

In the preferred embodiment the base layer 110 of the tape is woven from yarns of RPET and spandex. The yarns are preferably woven via a weft, twill, satin, plain or any other type of weave well known in the art of fabric production. The type of weave may create a symmetrical fabric (such as a plain weave) where the base layer comprises a face side 111 and back side 112 that are substantially similar at least visually. Preferably however the type of weave creates an asymmetric fabric (such as a twill weave) where the back 112 and face 111 sides are visually different.

As a further alternative, the base layer 110 is preferably composed of a combination of RPET, a fabric material and spandex. The base layer 110 is a woven layer with two sets of yarns or threads interlaced at right angles to form the base layer 110. The yarns or threads being composed of a combination of RPET, a fabric material and spandex. The fabric material forming intermittent placed threads between the RPET and spandex. The fabric material is any man-made or synthetic fibre which when added to the RPET and spandex ensures that the base layer will maintain a predetermined width while allowing a further increase in the elastic recoil of the tape.

Figure 2:
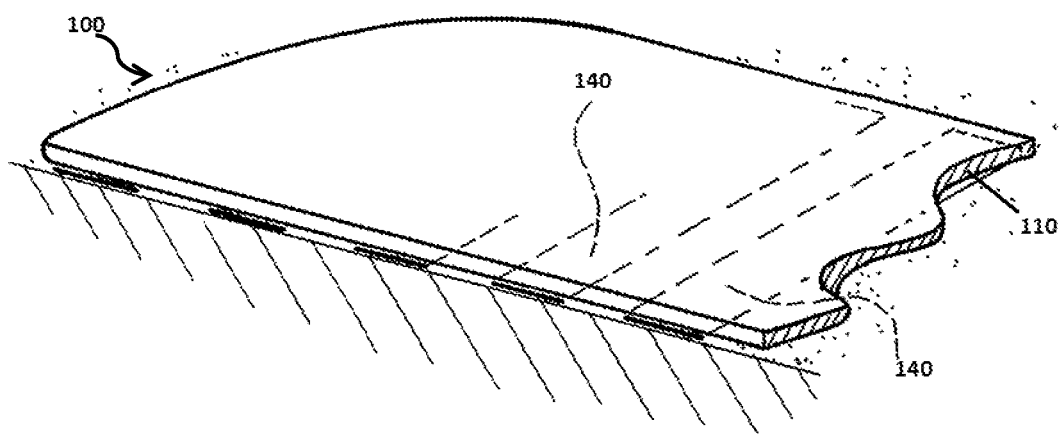
FIG. 2 is a perspective view of an alternative form therapeutic tape of the invention having adhesive strips.

The adhesive layer 120 may be applied to either back or face sides but in the preferred embodiment it is applied to the face side 111. In the asymmetric base layer case the ends of the fabric tend to curl towards the face side and hence application of the adhesive layer on this side will allow the adhesive side of the tape 100 to curl towards the user's skin at the ends to maintain stronger adhesion. The adhesive may be an acrylic based adhesive, or any other form well known in the art of tape technology and it may be applied/coated to the base layer 110 via any suitable well-known method. In the preferred embodiment a medical grade acrylic based adhesive is used. The adhesive may be a pressure and/or heat sensitive adhesive. The adhesive 120 may be applied evenly and uniformly over the entire or a substantial portion of the surface 111 of the base layer 110 or alternatively in regions or intervals such as in transverse and uniformly spaced strips 140 as shown in FIG. 2.

The preferred type of weave in combination with the elasticity of the base layer ensures that the tape sufficiently maintains its width (in the direction of the wefts) as it is stretched, to within approximately 80%-100% of the relaxed width. This ensures the tape continues to perform its required function as it dynamically stretches in use. If the tape narrows significantly it is hard to handle and get appropriate adhesion on the skin. It will also often curl at the edges of the tape.

Also, if the density of the fabric is too low it becomes too floppy and difficult to handle. In the preferred embodiment, the tape comprises a density of between approximately 100 gsm and approximately 400 gsm, more preferably between approximately 180 gsm and approximately 320 gsm, even more preferably between approximately 220 gsm and approximately 300 gsm, and most preferably between approximately 280 gsm and approximately 290 gsm.

Also, in a preferred embodiment, the tape comprises a base layer formed from a yarn of RPET of a grade of between approximately 50D and approximately 120D, more preferably between approximately 65D and approximately 105D and most preferably approximately 100D. Whilst the yarn of spandex in the base layer is of a grade of between approximately 20D and approximately 60D, more preferably between approximately 30D and approximately 50D and most preferably approximately 40D.

In the preferred embodiment a printed ink design is provided on the side of the base layer opposing the adhesive layer (see FIGS. 3-6). The printed ink design in addition to being aesthetic also improves the resistance and increases the elasticity of the tape 100.

Mechanical Properties

RPET has been found to be particularly useful for the application of therapeutic taping as it provides relatively high stiffness and exhibits a relatively high resistance to stretch at the early stages of stretch of the tape 100 compared to traditional therapeutic tapes. In combination with spandex, a viscoelastic material is formed comprising a resistance to stretch that is dependent on the rate of strain/stretch. As the rate of stretch is increased, the stiffness of the tape 100 is also increased. When applied on the skin with a muscle and/or associated tendon(s), this type of tape behaviour allows for sufficiently high levels of deceleration or load absorption during fast or powerful movements performed by the user, thereby protecting the underlying structures associated with the movement such as the ligaments and/or the musculotendinous units that are otherwise susceptible to injury or damage. Injuries often occur at times of fatigue, so by absorbing a higher portion of the load (due to the increased stiffness of the tape 100) the demand on the muscle is reduced. This in turn lowers metabolic demand and improves fatigue tolerance especially when the muscle is loaded repeatedly or cyclically.

Furthermore, tendinopathy is induced more rapidly in response to tensile and compressive loading and an affected or injured tendon will deform more when subjected to a given load. Therefore, by having an increased stiffness/elasticity modulus, the tape 100 can reduce demand on the musculotendinous unit and reduce tensile loading, protecting the tendons from injury. Pain perception is also reduced in the same manner.

Low elasticity will not provide the desired level of deceleration for supporting muscle and/or tendon movement as mentioned above and will not allow the tape to dynamically adjust its stretch in time with the user's activity. Kinesiology tapes for example are weak elastically and are designed to lift the skin and work on a physiological level rather than a mechanical one.

Whilst the tape 100 exhibits relatively high stiffness it is still elastic and sufficiently non-rigid. Rigidity will not help to absorb load and acts to restrict movement which will limit performance/movement of the user. In certain cases, reaction forces may be carried directly through the rigid tape onto other parts of the musculoskeletal or musculotendinous system injuring other parts of the user's body as movement is the body's way of dissipating load. For instance, if the ankle is locked up by a rigid tape, ground reaction forces will not dissipate and carry through to the knee, hip or lower back affecting that region of the user. Also, people with neurological deficit such as strokes often need strong assistance as they have very weak or ineffectual muscle contractions. Again, rigid tapes are not assistive at all and only loosen once load is applied to them.

The use of RPET provides the therapeutic tape 100 with a sufficiently high level of elasticity for giving the desired levels of deceleration particularly during the initial stretch zone, but low enough to allow for sufficient load absorption so not to promote the transfer of forces onto other parts of the system.

In some embodiments the tape is stretchable to approximately 190% of the relaxed length of the tape. In other embodiments the tape may be stretchable to approximately 140-180% of the relaxed length of the tape. When a muscle is lengthened it has a poorer capacity to generate force. This is called mechanical insufficiency. The mid-range length region of a muscle is where it can generate most force due to the optimal cross-linking of the actin and myosin filaments within the contractile tissue. Therefore it is advantageous to be able to assist in the outer range of muscle length and this is when the tape will be stretched the most in use. If the tape does not have sufficiently high elasticity it will either limit movement or come off and possibly cause a traction blister. If it stretches far enough to stay on but stretches beyond the elastic limit of the tape, the tape will lose its resistance very quickly so will not maintain its effect over a period of time or with cyclic loading. The inclusion of RPET in the base layer 110 helps achieve the desired levels of elasticity and elastic limit to allow for full range of motion when applied in use.

Figure 4:
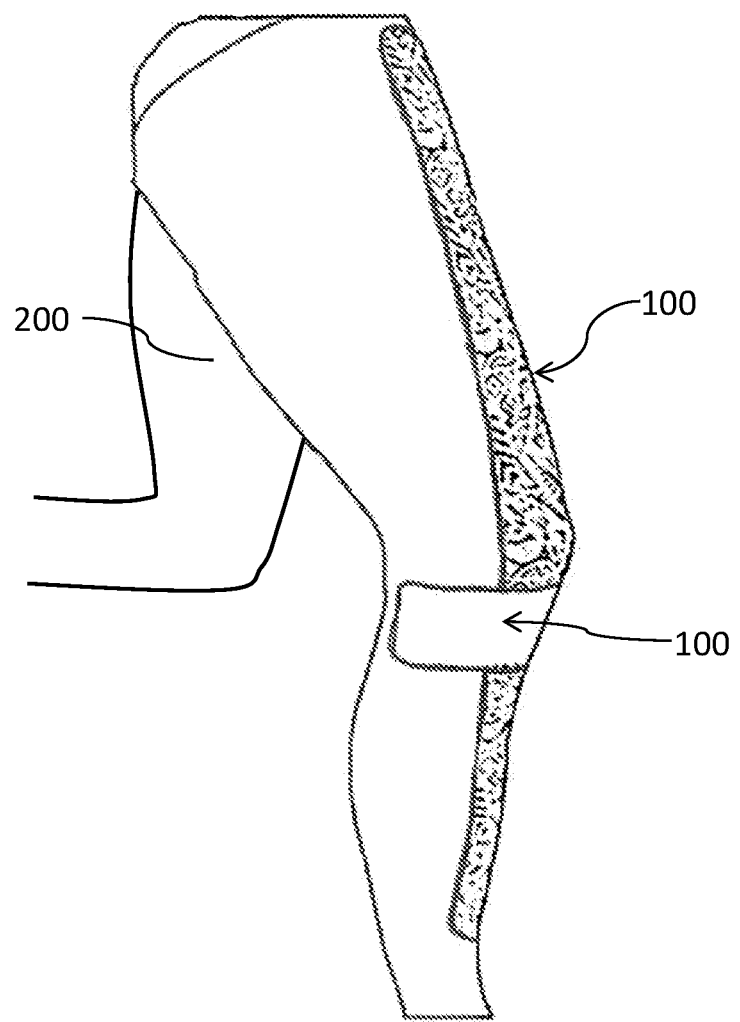
FIG. 4 is a perspective view of a preferred form therapeutic tape of the invention in use to support a user with tendonitis.

Some of the other benefits of RPET over virgin PET or traditional cotton or nylon based therapeutic tape fabric material include:

RPET provides more strength for a given density of fabric compared to virgin PET. This also means advantages in terms of the ability for moisture to escape the fabric, further reducing the weight which helps regulate the temperature and provide more comfort to the user by allowing the skin to breathe better to reduce incidents of skin reactions/contact dermatitis;

RPET adheres to itself well which is clinically beneficial when layers of tape are required to clinically treat a patient (see FIG. 4 for example). Layers of tape may be laminated together to increase force or resistance. Existing nylon products do not adhere well to themselves and often come off if taped in this way whereas the RPET based tape of the invention provides a good level of adhesion for achieving this clinically beneficial treatment technique;

RPET also provides environmental benefits during manufacture including reduction of water usage by approximately 90%, reduction of energy usage by 70% and the use of less harmful chemicals in comparison to virgin PET. Furthermore, RPET has an approximately 50% lower carbon footprint than organic cotton, 90% lower than nylon and 75% lower than other polyesters.

Applications of Use

The tape 100 is typically applied to the user's skin with the required muscle or musculotendinous unit in a preferably slightly shortened state. The tape is preferably applied to the skin of the user to extend beyond the origin and insertion regions of a muscle. When the therapeutic tape 100 is applied in a slightly stretched/tensioned state with the joint or muscle, the tape conveys a mechanical advantage and results in the tape stretching further and faster than the musculotendinous unit. During use, having the tape applied in the slightly tensioned state allows the tape to generate resistance as soon as movement of the associated musculotendinous unit occurs to help decelerate motion and reduce the eccentric demand on the muscle. Once deceleration is complete (the tape is in a substantially stretched position and the muscle is in an isometric or relaxed phase) energy becomes stored in the tape as elastic potential energy. This energy is then re-injected into the kinetic chain when the muscle transitions into the concentric phase to assist in movement of the muscle, particularly at low velocities. The tape is preferably applied to cross the joint in order to act on the levers (bones) that comprises that joint. The technique can target long lever muscle/force efficiency and elastic energy transfer in a sagittal plane by taping along the lever arm (assist or resist the gross movement) or facilitate the isometric stabilising role of the muscles to prevent excessive joint movement by taping across the joint axis. Both of these can be tied in to the angle of pennation of the target muscles. Taping circumferentially allows the strong elastic recoil to provide a compressive force to augment force closure.

Figure 3:
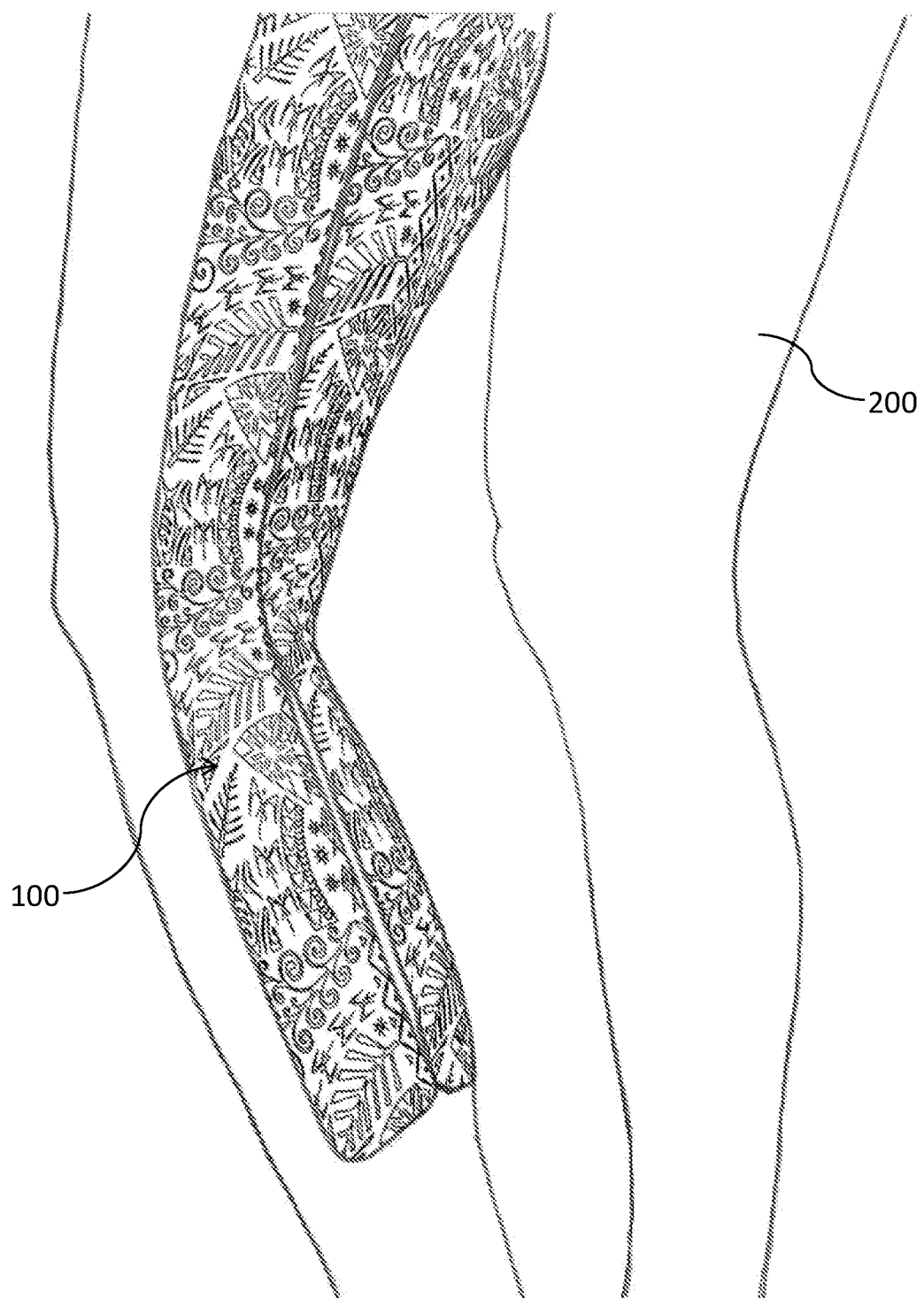
FIG. 3 is a perspective view of a preferred form therapeutic tape of the invention in use to support a user with a hamstring tear.

Referring to FIG. 3, an example application of the tape 100 is shown where the tape 100 is applied to a user 200 with a hamstring tear. The tape 100 is applied in a relatively short and slightly tensioned state with the muscle. The tape is preferably applied when the knee is at a flexion angle of approximately 120-130 degrees (rather than full flexion) so that knee extension is not resisted greatly throughout the initial stages of extension, when the quadriceps muscle is extending the knee to generate force to kick a ball for example. A deceleration effect is created by the tape as it lengthens with extension of the knee to reduce the eccentric demand on the hamstring muscles which act to slow the rate of swing of the leg down. When the user places their foot on the ground and begins to pull themselves over the top of their foot, the tape is at a lengthened and tensioned stage and full of elastic potential energy. This energy assists in the transition back into flexion and into the short and slightly tensioned state of the tape.

The technique shown in FIG. 3 may be indicated for hamstring muscle strain/tear/tendinopathy and to assist the action of weak hamstring muscles or to decelerate knee extension. When taping for the hamstrings the tape extends to the distal calf, well beyond the insertion of the hamstrings into the fibular head and proximal tibia. When the tape is applied with stretch and with the knee in flexion, this increased distance from the axis of rotation will result in the tape stretching further and faster than the hamstrings musculo-tendinous unit (MTU).

Referring to FIG. 4, another example of clinical use of the tape 100 is with patients who have patella tendinopathy (tendonitis) which is caused by an increase in load beyond the tendon's capacity to dissipate and adapt to that load. The tape 100 can be placed from the mid to upper thigh across the knee to the mid shin level with the knee fully extended when the tape is in the relatively short length and slightly stretched state. As the patient 200 attempts to squat, the stretch on the tape increases and resists the knee from collapsing into complete flexion. This will reduce the eccentric workload on the quadriceps muscle required to control flexion. This will also reduce the load through the patella tendon.

This technique may be indicated for quads muscle strain/tear, patella tendinopathy (jumper's knee), Osgood-Schlatter's disease, fat pad syndrome, patellofemoral pain syndrome, restless legs syndrome, poor quads control post knee surgery e.g. total knee replacement or ACL repair.

Further the tape 100 is configured to be applied directly over the patella, instead of around the patella as in traditional tapes which does not create the same leverage effect and pulley effect that can be obtained by going directly over the patella. The high elasticity and two dimensional stretch means the tape 100 can be applied over the patella which does not create restriction to movement and potential compressive forces at the patella-femoral joint. This further tape is sometimes referred to as a 'pinch' offload strip which can be directed towards the tendon or fat pad as shown or moved to the tibial tuberosity for Osgood-Schlatter's disease. This gathers all of the soft tissue to create a soft, spongy area to reduce firing of peripherally sensitized nociceptors.

Figure 5:
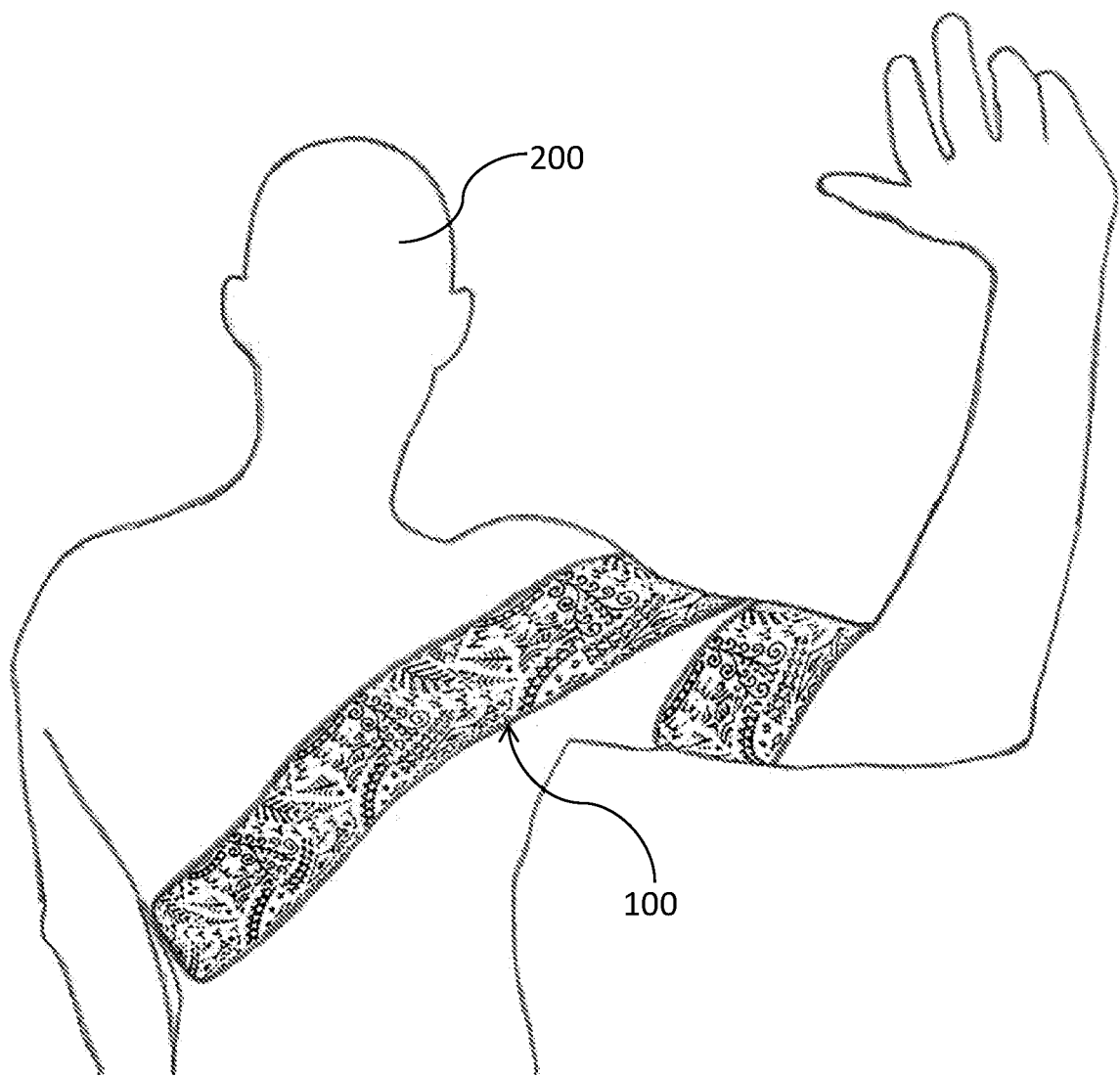
FIG. 5 is a perspective view of a preferred form therapeutic tape of the invention in use to support a user with a shoulder injury.

Referring to FIG. 5, another example of the tape 100 in use is to assist a user 200 in throwing a device such as a ball. The tape can be applied in a spiral form around the arm and then across the back of the shoulder joint associated with the arm, below the acromion and then obliquely across the back towards the opposing hip. The tape 100 is applied with the arm in abduction to 90 degrees, horizontal extension and external rotation with slight tension applied to the tape. As the arm swings through the tape will stretch and resist the follow through movements into horizontal flexion, extension and internal rotation along with trunk rotation. It is applied in the relatively short length and slightly stretched state so that it begins to stretch strongly just after ball release (and not prematurely during the acceleration phase). This deceleration aims to reduce the intrinsic muscle force required to decelerate the motion as well as some of the high distraction forces on other structures such as the posterior capsule. It is also designed to give a superiorly directed force (approximation) and to correct the scapula position to take some of the weight of the arm (reduce load and work requirements) and to improve the length tension relation of the scapula and rotator cuff muscles (i.e. bring them into a more mid-range position rather than being on stretch where they have a poor capacity to generate force). This example is sometimes referred to as a 'shoulder external rotation spiral technique' which is indicated for pain during deceleration in throwing or hitting, some rotator cuff or subacromial impingement syndromes or to encourage external rotation at the shoulder.

Figure 6:
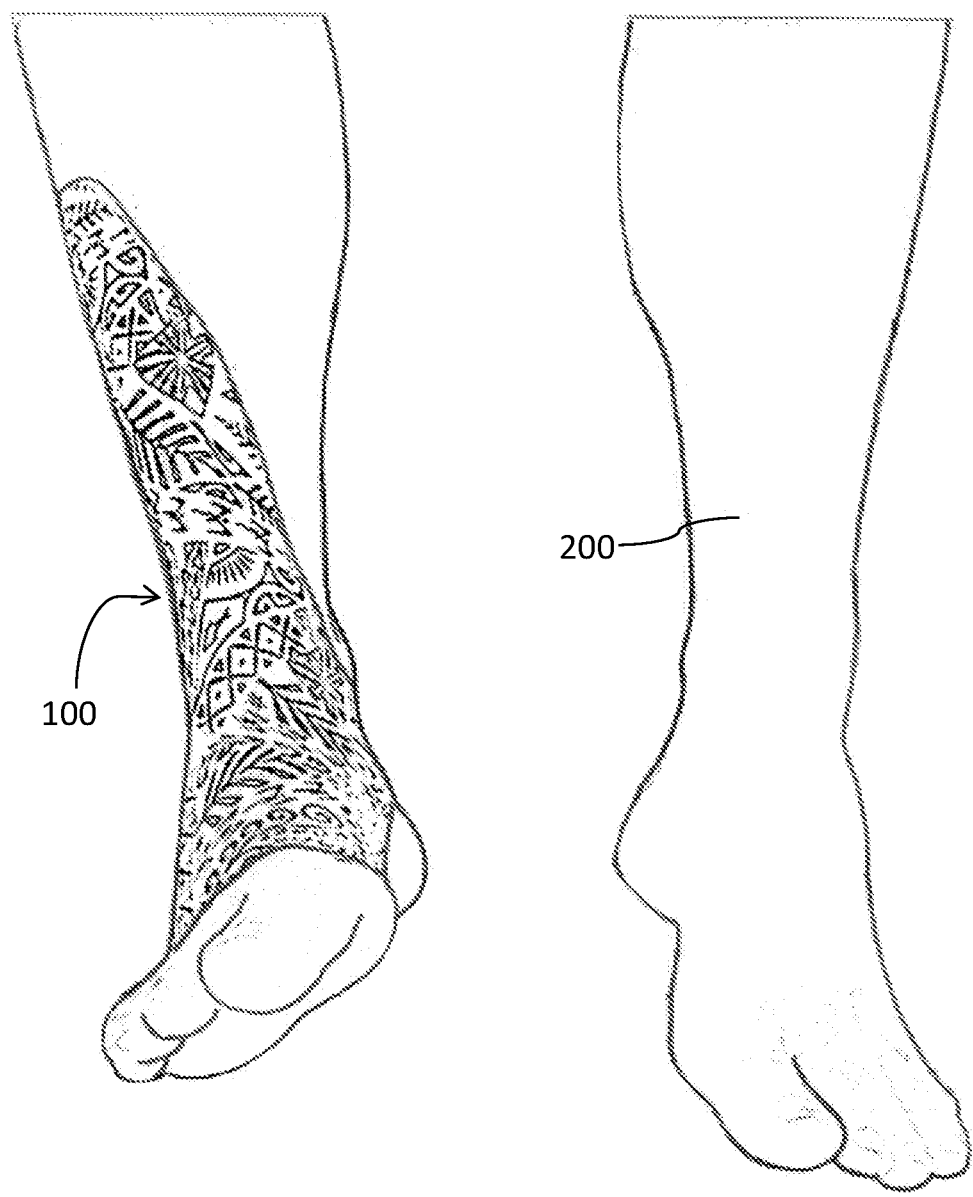
FIG. 6 is a perspective view of a preferred form therapeutic tape of the invention in use to alleviate foot drop.

Referring to FIG. 6, another example of the tape 100 in use is in the application of foot drop. It is desirable not to lock movement as movement within the foot and at the ankle is important for balance, accommodating to the ground surface and for gait. However if someone has a foot drop they may be placed in a splint or rigid tape to stop the foot dropping into plantar flexion and the toes catching on the ground which can lead to falls. It also restricts the normal motion of dorsiflexion and plantar flexion required for gait. This is a passive restriction of movement and results in ground reaction forces being carried through to the knee, hip or lower back affecting that region of the user. A strongly elastic tape can still resist the effect of gravity so reduce the degree of plantar flexion but still allows the foot and ankle to move. Furthermore as the person moves over the effected foot during gait they move into a plantar flexed position just prior to toe off (depending on the level of function of various muscles). This stretches the tape and stores the elastic potential energy so that as the toe is lifted from the ground the energy is released to help spring the foot into dorsiflexion and therefore reduce the chance of the toe catching. It allows for a more natural gait pattern with less compromise of balance, gait etc. Low elasticity does not have sufficient resistance against gravity.

Experimentation and Results

A test was conducted to compare the elasticity of different therapeutic tapes on the market and of the preferred form therapeutic tape of the invention comprising approximately 85% RPET and 15% spandex. The results are shown in table 1 below.

A 150 mm relaxed length and 50 mm relaxed width sample of each type of tape was taken and it's resistance to stretch was measured by suspending a weight at an end of the tape sufficient to achieve a desired stretch length. The tapes all had similar widths and their change in width over stretch was also determined. Three types of Nylon based tapes were compared to the RPET based tape of the invention.

It can be seen that the RPET tape provides relatively higher resistance to stretch (elasticity modulus) than the other tapes on the market with one of the current tapes on the market (kinesiology) having a shorter stretch limit than the remaining tapes.

TABLE 1

Test Results for Resistance vs. Stretch of different types of therapeutic tapes

| Sample (50 mm × 150 mm) | 200 mm Stretch | | 220 mm Stretch | | 240 mm Stretch | |
|---|---|---|---|---|---|---|
| | Resistance (g) | Width (mm) | Resistance (g) | Width (mm) | Resistance (g) | Width (mm) |
| Nylon 1 | 400 | 42 | 440 | 42 | 600 | 39 |
| Nylon 2 | 420 | 45 | 645 | 42 | 705 | 40 |
| Nylon 3 | 715 | 45 | 900 | 43 | 1300 | 42 |
| RPET | 1020 | 45 | 1300 | 42 | 1700 | 40 |
| Kinesiology (cotton/spandex) | 150 | 49 | 200 | 49 | Insufficient elongation | Insufficient elongation |

Figure 7:
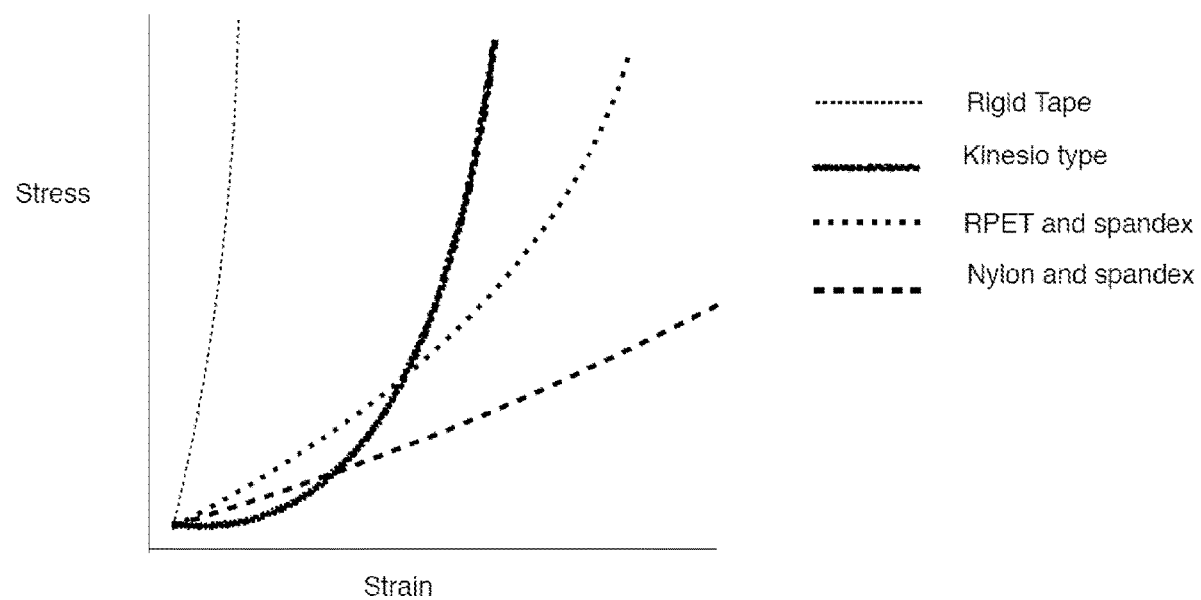
FIG. 7 is a graph showing the stress vs. strain performance of various types of therapeutic tapes.

Referring to FIG. 7 a graph of the stress vs. strain performance of various types of therapeutic tapes is shown. It can be seen from the graph that the rigid tape has very little elongation despite high forces being applied which would significantly restrict or block movement of the muscles and joints. The kinesiology type tape has approximately 140% elongation/elastic limit length but a small amount of elastic resistance at the initial stages of stretch and a very high/rigid resistance performance at the final stages of stretch. The Nylon and spandex tape elongates much more under lower loads which means it provides too little resistance to motion. Finally the RPET and spandex tape has:

a much higher resistance at the initial stages of stretch than the kinesiology type and nylon based tapes (yet still more elastic than the rigid tape), continues to stretch past the elastic limit of the kinesiology type tape to permit movement, and unlike the nylon based tape, maintains a relatively high resistance during the upper zones of stretch to ensure sufficient levels of deceleration and load absorption.

Advantages

The present invention provides a number of advantages over what is currently in use for therapeutic adhesive tape for use in medical or sporting applications. The present tape is a biomechanical tape it is not a kinesiology tape.

The therapeutic tape is a 4-way stretching tape with strong elastic recoil that absorbs force to reduce the workload on the body. The therapeutic tape can be applied using methods which aim to directly manage load, modify movement patterns and assist function. Whether the tape is applied to support fatigued or injured body parts, or to improve technique while still allowing 100% range of motion, the user will see and feel the difference when the therapeutic tape in accordance with the present invention is used.

In order to achieve these advantages a tape has been devised which is composed of a synthetic, stretch nylon and lycra cloth compared to that of known tapes that are predominantly cotton. The tape is designed to stretch in all direction (4-way stretch) while known tapes are designed to stretch longitudinally (2-way stretch). The therapeutic tape of the present invention has many times the resistance and recoil, likened to a bungee cord. The tape can stretch to over 200% of its resting length with no restrictive end point, unlike known tapes which have a defined rigid end point where the tape will stretch no more. This prevents the tape from being applied with the body part in a shortened position while maintaining full range.

The tape of the present invention has been designed to work mechanically, designed to alter movement patterns while absorbing load and re-injecting that energy back into movement, all without limiting range of motion. The therapeutic tape of the present invention is about managing load, managing movement patterns, and managing function by introducing force into the system.

The therapeutic tape is an externally applied load absorbing product that affects the work of muscles and motion of joints.

The present invention has been specifically developed to provide strong mechanical assistance externally to reduce the work on injured tissues, assist weak muscles, improve movement patterns, augment stability via force closure mechanism, change position to improve the muscle's capacity to generate force (length-tension relationship) all while still allowing full range of motion even when performing complex, multi-planar movements like those required in sport or work.

The foregoing description of the invention includes preferred forms thereof. Modifications may be made thereto without departing from the scope of the invention as defined by the accompanying claims.

The invention claimed is:

1. A therapeutic tape configured to be applied to the skin of a user, the tape comprising: a base layer having a face side and a back side, the base layer being composed of a combination of recycled polyethylene terephthalate (hereinafter: RPET) and an elastic material, wherein the base layer comprises between 70% and 95% by weight of RPET; and an adhesive layer deposited on one of said face side or back side of the base layer configured to attach the tape to the skin of the user, wherein the base layer is configured to maintain a predetermined width whilst allowing an increase in elastic recoil.

2. A therapeutic tape as claimed in claim 1 wherein the tape is stretchable along at least two dimensions.

3. A therapeutic tape as claimed in claim 2 wherein the tape is stretchable in both directions along a longitudinal axis of the tape and stretchable in both directions along a transverse axis of the tape.

4. A therapeutic tape as claimed in any one of the preceding claims wherein the tape is stretchable to 190% of a relaxed length of the tape.

5. The therapeutic tape of claim 1, wherein the base layer is woven.

6. A therapeutic tape as claimed in claim 1 wherein the tape further comprises a release liner configured to cover an exposed surface of the adhesive layer when the tape is not in use.

7. A therapeutic tape as claimed in claim 1 wherein the base layer comprises of a density of between 180 gsm and 320 gsm, between 220 gsm and 300 gsm; or between 280 gsm and 290 gsm.

8. A therapeutic tape as claimed in claim 1 wherein the base layer comprises between 80% and 90% by weight of RPET; or 83% by weight of RPET.

9. A therapeutic tape as claimed in claim 1 wherein the elastic material comprises spandex.

10. A therapeutic tape as claimed in claim 9 wherein the base layer comprises between 5% and 30% by weight of spandex; between 10% and 20% by weight of spandex; or 17% by weight of spandex.

11. A therapeutic tape as claimed in claim 1 wherein the base layer comprises a printed ink design deposited on the opposite side of the base layer to the deposited adhesive layer, and configured to be exposed in use.

12. The therapeutic tape of claim 1, wherein the base layer is in the form of a twill style textile weave.

13. The therapeutic tape of claim 12, wherein the twill style textile weave is weft woven.

14. The therapeutic tape of claim 1, wherein the tape is in the form of an elongate strip configured to be wound into a roll for storage prior to use and from which a length of tape may be cut for application to the user.

15. The therapeutic tape of claim 1, wherein the layer of adhesive is deposited on the face side of the base layer.

16. A method of manufacturing a therapeutic tape comprising the steps of: forming a base layer of fabric by weaving a recycled polyethylene terephthalate (RPET) material with an elastic material, and depositing a layer of adhesive on either a face side or a back side of the formed base layer configured to attach the tape to skin, wherein the base layer comprises between 70% and 95% by weight of RPET, wherein the base layer is configured to maintain a predetermined width whilst allowing an increase in elastic recoil.

17. A method as claimed in claim 16 further comprising the step of adhering a release liner on the layer of adhesive for covering the layer of adhesive, and/or wherein the step of weaving comprises weft weaving the RPET material with the elastic material.

18. A method as claimed in claim 16 further comprising the step of printing an ink on a side of the base layer opposing the side to which the adhesive is deposited, and/or further comprising the step of winding the tape onto a roll.

19. A therapeutic tape configured to be applied to the skin of a user, the tape comprising: a base layer having a face side and a back side, the base layer being a woven layer with two sets of yarns or threads interlaced at right angles to form the base layer, the yarns or threads being composed of a combination of recycled polyethylene terephthalate (hereinafter: RPET), a fabric material and an elastic material, and an adhesive layer deposited on one of said face side or back side of the base layer configured to attach the tape to the skin of the user, wherein the base layer comprises between 70% and 95% by weight of RPET, wherein the base layer is configured to maintain a predetermined width whilst allowing an increase in elastic recoil.

20. A therapeutic tape as claimed in claim 19, wherein the fabric material consists of intermittent threads interlaced into the base layer between the RPET and the elastic material, the threads of fabric material ensure that the base layer maintains the predetermined width while allowing the increase in the elastic recoil of the tape.

21. A therapeutic tape of claim 19, wherein the fabric material comprises man-made or synthetic fibres.

* * * * *